United States Patent
Francis et al.

(10) Patent No.: US 10,814,079 B2
(45) Date of Patent: Oct. 27, 2020

(54) DEVICE FOR NASAL SPRAYING OF FLUID PRODUCT

(71) Applicant: UNIVERSITÉ DE TOURS, Tours (FR)

(72) Inventors: Mirvatte Francis, Longpont sur Orge (FR); Laurent Vecellio-None, Chambray les Tours (FR)

(73) Assignee: UNIVERSITE DE TOURS, Tours (FR)

( * ) Notice: Subject to any disclaimer, the term of this patent is extended or adjusted under 35 U.S.C. 154(b) by 340 days.

(21) Appl. No.: 15/507,977

(22) PCT Filed: Sep. 1, 2015

(86) PCT No.: PCT/FR2015/052306
§ 371 (c)(1),
(2) Date: Mar. 1, 2017

(87) PCT Pub. No.: WO2016/034803
PCT Pub. Date: Mar. 10, 2016

(65) Prior Publication Data
US 2017/0304568 A1    Oct. 26, 2017

(30) Foreign Application Priority Data

Sep. 2, 2014  (FR) .................................... 14 58181

(51) Int. Cl.
*A61M 15/08* (2006.01)
*A61M 15/00* (2006.01)
(Continued)

(52) U.S. Cl.
CPC .......... *A61M 15/08* (2013.01); *A61M 11/001* (2014.02); *A61M 11/005* (2013.01);
(Continued)

(58) Field of Classification Search
CPC ................ A61M 15/08; A61M 15/002; A61M 15/0098; A61M 15/0065; A61M 15/009;
(Continued)

(56) References Cited

U.S. PATENT DOCUMENTS 2,101,175 A * 12/1937 Gustafsson ........... B05B 7/0815
239/8
2,772,117 A   11/1956 Ritzau et al.
(Continued)

FOREIGN PATENT DOCUMENTS

DE     1 625 238 A1    6/1970
EP     1 023 911 A2    8/2000
(Continued)

OTHER PUBLICATIONS

International Preliminary Report on Patentability, dated Apr. 6, 2017, from the International Bureau in counterpart International application No. PCT/FR2015/052306.
(Continued)

*Primary Examiner* — Timothy A Stanis
*Assistant Examiner* — Thao Tran
(74) *Attorney, Agent, or Firm* — Sughrue Mion, PLLC

(57) ABSTRACT

A nasal fluid-spray device having: a reservoir containing at least one dose (D) of fluid; and a dispenser system that, each time the device is actuated, sprays a dose (D) of fluid through a spray orifice, generating a spray that extends axially from the spray orifice. The device further includes a generator system for generating a secondary flow, which generator system is actuated simultaneously with the dispenser system, the secondary flow generator system having a secondary flow channel provided with an outlet orifice, the outlet orifice arranged downstream from the spray orifice, and the secondary flow extending from the outlet orifice along an axis (B) that forms an angle (α) relative to the axis
(Continued)

(A) of the spray and that intersects the axis (A), thereby deforming and/or deflecting the spray.

21 Claims, 8 Drawing Sheets

(51) Int. Cl.
    *A61M 11/00* (2006.01)
    *A61M 11/08* (2006.01)
(52) U.S. Cl.
    CPC ........ *A61M 11/007* (2014.02); *A61M 15/002* (2014.02); *A61M 15/009* (2013.01); *A61M 15/0065* (2013.01); *A61M 15/0091* (2013.01); *A61M 15/0098* (2014.02); *A61M 11/08* (2013.01); *A61M 2202/064* (2013.01); *A61M 2205/071* (2013.01); *A61M 2205/073* (2013.01); *A61M 2210/0681* (2013.01)
(58) Field of Classification Search
    CPC ............ A61M 15/0091; A61M 11/001; A61M 11/007; A61M 11/005; A61M 11/08; A61M 2202/064; A61M 2205/071; A61M 2205/073; A61M 2201/0681; A61M 11/00; A61M 11/006–008; A61M 11/06; A61M 2210/0681; B05B 7/08; B05B 7/0807; B05B 7/0815; B05B 7/0491; B05B 7/06; B05B 7/061; B05B 12/18
    See application file for complete search history.

(56) References Cited

U.S. PATENT DOCUMENTS

| | | | | |
|---|---|---|---|---|
| 3,970,249 | A * | 7/1976 | Singer | B05B 7/0861 239/102.1 |
| 5,996,576 | A * | 12/1999 | Yule | B05B 7/0807 128/203.12 |
| 6,729,334 | B1 * | 5/2004 | Baran | B67D 7/06 128/207.14 |
| 8,899,229 | B2 * | 12/2014 | Djupesland | A61M 15/0028 128/203.15 |
| 2004/0079360 | A1 * | 4/2004 | Coffee | A61M 15/008 128/200.14 |
| 2007/0039614 | A1 * | 2/2007 | Djupesland | A61M 16/0495 128/200.23 |
| 2010/0030188 | A1 | 2/2010 | Xia | |
| 2011/0023869 | A1 * | 2/2011 | Djupesland | A61M 15/0028 128/200.14 |
| 2011/0088690 | A1 * | 4/2011 | Djupesland | A61M 11/02 128/200.23 |
| 2011/0114087 | A1 * | 5/2011 | Djupesland | H01M 4/861 128/200.14 |
| 2013/0142868 | A1 * | 6/2013 | Hoekman | A61M 15/009 424/450 |
| 2014/0073562 | A1 * | 3/2014 | Djupesland | A61M 15/08 514/4.8 |
| 2014/0083424 | A1 * | 3/2014 | Hoekman | B05B 7/08 128/203.22 |
| 2016/0114112 | A1 * | 4/2016 | Riebman | A61M 11/02 604/500 |
| 2019/0269867 | A1 * | 9/2019 | Djupesland | A61M 15/009 |

FOREIGN PATENT DOCUMENTS

| | | |
|---|---|---|
| WO | 02/068031 A2 | 9/2002 |
| WO | 03/026559 A2 | 4/2003 |
| WO | 2012/024595 A2 | 2/2012 |

OTHER PUBLICATIONS

International Search Report of PCT/FR2015/052306, dated Jan. 8, 2016. [PCT/ISA/210].

* cited by examiner

DEVICE FOR NASAL SPRAYING OF FLUID PRODUCT

CROSS-REFERENCE TO RELATED APPLICATIONS

This application is a National Stage of International Application No. PCT/FR2015/052306 filed Sep. 1, 2015, claiming priority based on French Patent Application No. 1458181, filed Sep. 2, 2014, the contents of all of which are incorporated herein by reference in their entirety.

BACKGROUND

Technical Field

The present invention relates to a nasal spray device for spraying a fluid, in particular a pharmaceutical fluid.

SUMMARY

The nasal cavities are separated longitudinally by the septum. Each of the nasal cavities is made up firstly of the nose and then of a nasal valve. The nasal valve has a particular shape. It extends over about 1 centimeter (cm) in depth, has a vertical longitudinal section of about 3 cm to 4 cm, and a width of about 1 millimeter (mm) to 3 mm. Beyond the nasal valve, the nasal cavities are made up of a larger cavity (about 7 cm in height by 2 cm to 3 cm in width). The conchae face the nasal valve. The roof of the nasal cavity is situated above the conchae, which roof includes the ethmoid sinuses, the olfactory bulb, and the olfactory nerve. FIG. 3, which is an image of a nasal-cavity anatomical model, shows the nose 1, the nasal valve 2, the conchae 3, and the ethmoids 4.

Nasal spray devices for spraying pharmaceutical fluid are well known in the state of the art. Such devices generate a rectilinear spray with a solid angle that penetrates axially into the user's nostril, as can be seen in FIG. 1 (which is a diagram showing a prior-art nasal spray). FIG. 1 shows a major drawback of prior-art devices. Specifically, since the nasal spray device 100 is not very invasive, if at all, the device does not go past the nasal valve 2. Thus, as a result of the anatomy of the nasal valve 2 and of the protective location of the conchae 3, the axial or rectilinear path of the spray particles does not make it possible to reach the roof of the nasal cavity, and in particular the ethmoids 4.

Documents WO 03/026559, WO 02/068031, and WO 2012/024595 disclose prior-art devices. The device in document WO 03/026559 uses a vortex movement of the path of the particles in order to improve distal targeting of nasal cavities. That system requires fine particles of about 2 micrometers (µm) to 50 µm. The system in document WO 02/068031 also uses fine particles (aerosol) in order to improve targeting of the ethmoid sinuses while limiting the pulmonary deposition by synchronizing the generation of aerosol with the patient exhaling. Document WO 2012/024595 describes a peripheral flow of air that rotates in a spiral and that axially surrounds the spray in order to entrain it, without however deflecting it from its axial direction. The cone of the spray thus remains symmetrical about its axial direction.

Those prior-art devices are difficult to implement, and in particular they require standard nasal spray devices to be modified substantially. In addition, the use of fine particles poses the problem of the total effectiveness of the deposition in nasal cavities. Specifically, a portion of the fine particles is generally not deposited in any of the nasal cavities (see in particular the publication entitled "Nasally inhaled pulsating aerosols: lung, sinus and nose deposition" by W. Moller, G. K. Saba, K. Haussinger, S. Becker, M. Keller, U. Schuschnig, Rhinology, August 2011; 49(3):286-91), thereby making the device and thus the medical treatment less effective.

An object of the present invention is to provide a nasal fluid-spray device that does not have the above-mentioned drawbacks.

Another object of the present invention is to provide a nasal fluid-spray device that improves the dispensing of the fluid sprayed into the user's nostril.

Another object of the present invention is to provide a nasal fluid-spray device that is simple and inexpensive to manufacture and to assemble.

The present invention thus provides a nasal fluid-spray device comprising: a reservoir containing at least one dose of fluid; and a dispenser system that, each time the device is actuated, sprays a dose of fluid through a spray orifice, generating a spray that extends axially from said spray orifice; said device further comprising a generator system for generating a secondary flow, which generator system is actuated simultaneously with said dispenser system, said secondary flow generator system comprising a secondary flow channel that is provided with an outlet orifice, said outlet orifice being arranged downstream from said spray orifice in the axial direction of said spray, and said secondary flow extending from said outlet orifice along an axis B that forms an angle relative to the axis A of said spray and that intersects said axis A, thereby deforming and/or deflecting said spray.

Advantageously, said secondary flow of said secondary flow generator system is formed by an external source of gas, in particular compressed gas.

In a variant, said secondary flow of said secondary flow generator system is formed by the user inhaling.

Advantageously, said secondary flow of said secondary flow generator system is made up of gas, in particular of air.

In a variant, said secondary flow of said secondary flow generator system comprises gas, in particular air, mixed with fluid, in particular particles of powder.

Advantageously, said angle α lies in the range 10° to 90°, advantageously in the range 20° to 80°, preferably in the range 30° to 70°, in particular about 35°.

Advantageously, the diameter of said spray orifice is substantially identical to the diameter of said outlet orifice, advantageously equal to about 2 mm.

In a variant, the diameter of said spray orifice is less than the diameter of said outlet orifice.

Advantageously, the diameter of said spray orifice is 0.3 mm and the diameter of said outlet orifice is 0.4 mm.

Advantageously, said secondary flow channel of said secondary flow generator system includes an inlet orifice.

Advantageously, said inlet orifice is connected to a source of gas, in particular of air, that is compressed.

In a variant, said inlet orifice is connected to the atmosphere.

Advantageously, said fluid is a medication in powder form.

In a variant, said fluid is a medication in liquid form.

Advantageously, said spray is composed of particles having a diameter that lies in the range 1 µm to 500 µm.

Advantageously, said secondary flow deforms and/or deflects said spray sideways in the user's nostril.

Advantageously, during actuation, said spray orifice is inserted into the nostril to a depth that lies in the range 15 mm to 30 mm.

Advantageously, for a man model, at least 10%, advantageously about 50%, of the spray is deposited on the ethmoids.

Advantageously, for a woman model, at least 2%, advantageously about 20%, of the spray is deposited on the ethmoids.

BRIEF DESCRIPTION OF THE DRAWINGS

These characteristics and advantages and others appear more clearly from the following detailed description, given by way of non-limiting examples, and with reference to the accompanying drawings, and in which.

DETAILED DESCRIPTION

Figure 1:
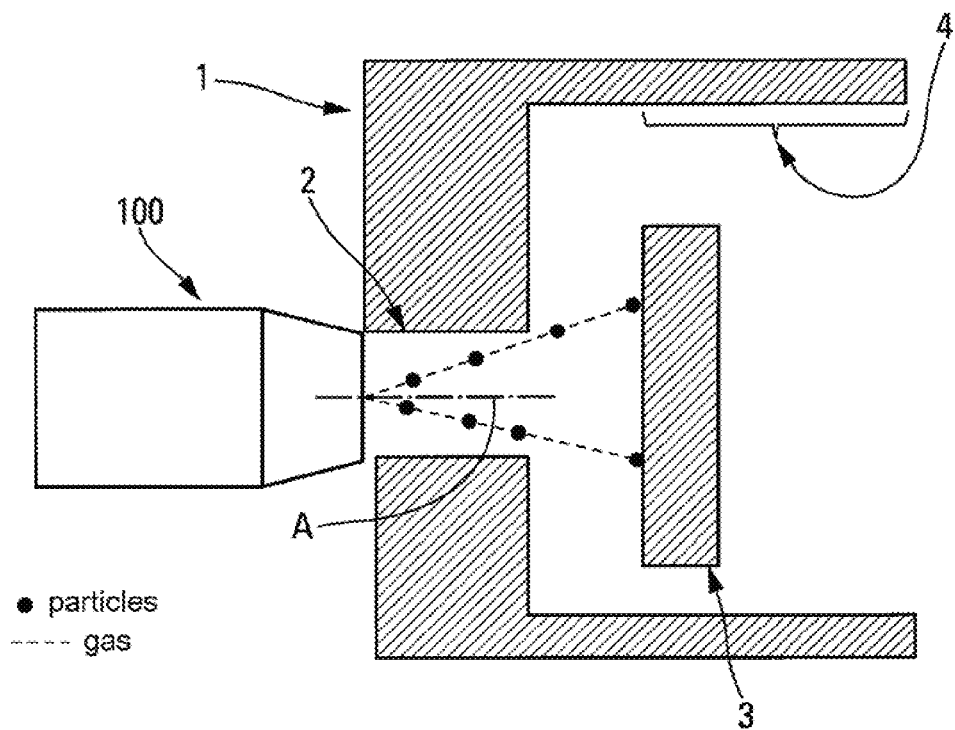
FIG. 1 is a very diagrammatic view of a nasal spray made with a prior-art nasal spray device.

In the description, the term "axial" refers to the longitudinal and rectilinear direction of the spray such as it is expelled through the spray orifice of the device, i.e. the axis A in the figures.

The invention applies more particularly to nasal spray devices of the single-dose type (device that dispenses only a single dose) or of the two-dose type (device that dispenses only two doses), but it could also apply to a multi-dose device (device that dispenses more than two doses). Such a nasal spray device generally includes a reservoir containing one, two, or more doses of fluid to be dispensed by nasal spraying.

For a single-dose device, a single dose is dispensed by a single actuation of the device. For a two-dose device containing two doses, and multi-dose devices containing more than two doses, the doses are dispensed successively during successive actuations of the device.

A dispenser system, which may be a pump, an aerosol valve, a piston sliding in the reservoir, or an air expeller, is generally used to transfer a dose, on each actuation, towards a spray orifice that is preferably arranged at the axial end of a nasal spray head.

The dispenser system may generate the spray, e.g. by generating an aerosol of a powder or a liquid in a flow of air or of gas.

In a variant, the spray head may include a spray profile that is provided immediately upstream from said spray orifice, and that generates a spray through said spray orifice. The spray profile may be of any appropriate type, e.g. with non-radial channels leading towards a swirl chamber that is directly connected to said spray orifice, thus causing the fluid to swirl just before it is expelled in spray form through said spray orifice. It should be observed that such a spray profile upstream from the spray orifice is not essential, and that the spray may be generated in any appropriate manner at said spray orifice or upstream therefrom.

The spray generated in this way is expelled through said spray orifice along an axial direction, and generally presents a symmetrical-cone shape that flares away from said spray orifice.

In the invention, the nasal spray device is suitable for depositing a quantity of fluid in various zones of the nasal cavities, and more particularly on the roof of the nasal cavities, in particular including the ethmoids, the olfactory bulb, and the olfactory nerve. To do this, the device of the invention includes firstly a dispenser system 20 that, each time the device is actuated, sprays a dose D of fluid through a spray orifice 35, generating a spray that extends axially from said spray orifice 35. Secondly, the device includes a secondary flow generator system 40 that is actuated simultaneously with said dispenser system 20. The secondary flow generator system 40 comprises a secondary flow channel 41 that is provided with an outlet orifice 45. In the invention, said outlet orifice 45 is arranged downstream from said spray orifice 35 in the axial direction of said spray, and said secondary flow extends from said outlet orifice 45 along an axis B that forms an angle α relative to the axis X of said spray and that intersects said axis A of said spray, thereby deforming and/or deflecting said spray. Preferably, the nasal spray device is oriented in appropriate manner relative to the nostril, so as to enable the particles of spray to reach the targeted zones. Optionally, orientation means may be provided so as to encourage the user to insert the device in the nostril with the correct orientation.

Figure 2:
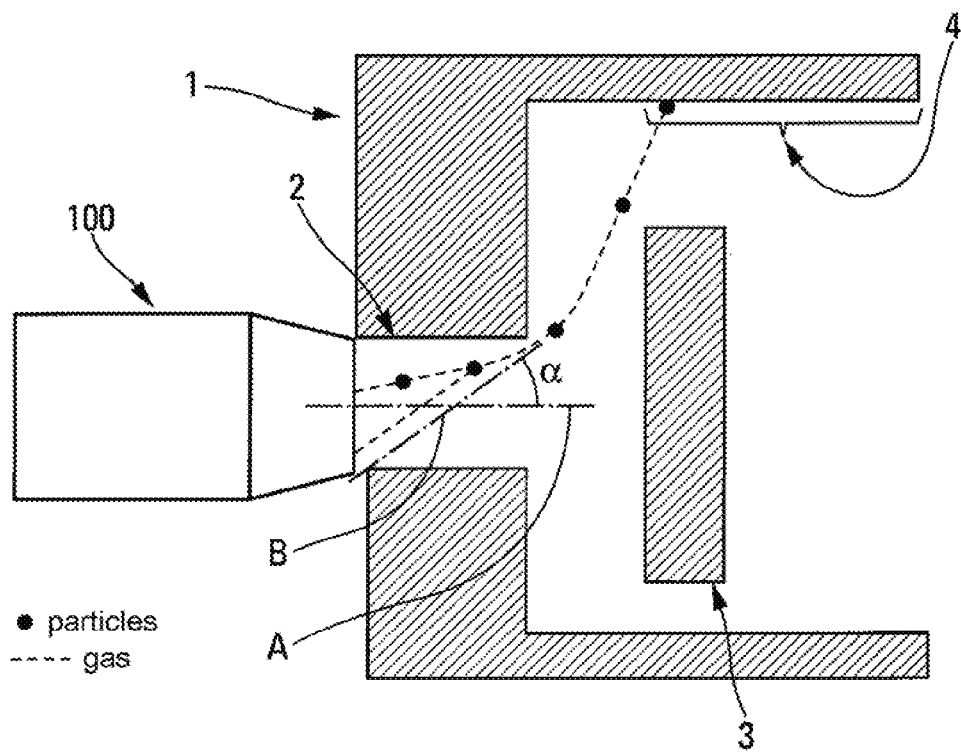
FIG. 2 is a view similar to the view in FIG. 1 showing nasal spraying performed with a nasal spray device of the present invention.
Figure 3:
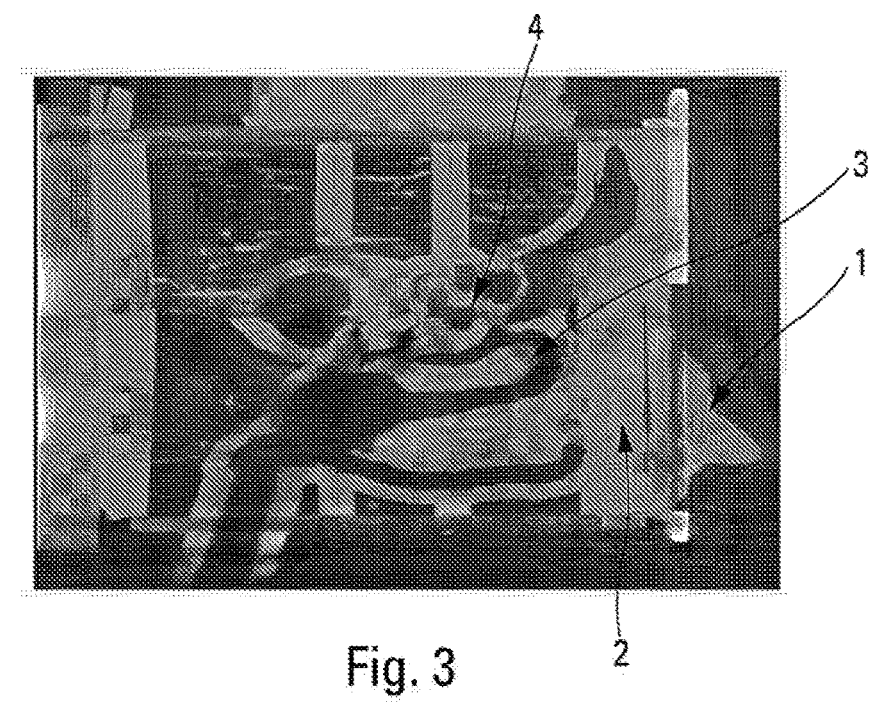
FIG. 3 is a diagrammatic view showing imaging of an anatomical model of a nasal cavity.

The device of the invention thus includes a first generator that produces particles with a substantially rectilinear initial speed, and a second generator, which may be active or passive, that generates a secondary flow, making it possible to deflect the rectilinear path of the aerosol after it has been generated. The second generator is positioned downstream from the first generator (in the dispensing direction), so that it acts on the spray only after said spray has been expelled from the spray orifice 35. The idea consists in obtaining a non-rectilinear path for the spray particles, in order to go past the conchae and reach the ethmoids, as shown diagrammatically in FIG. 2. The secondary flow interacts with the path of the particles of the spray, so as to deflect them, in particular along a path that extends upwards in the orientation in FIG. 2. Thus, said spray, which is substantially symmetrical about the axis A when it leaves the spray orifice 35, is deformed and/or deflected by said secondary flow so that it becomes asymmetric, which distinguishes the present invention from the prior art, and in particular from document WO 2012/024595.

The angle α formed between the path of the secondary flow (axis B) and the path of the particles of the spray produced by the first generator (axis A) advantageously lies in the range 10° to 90°, in particular in the range 20° to 80°, preferably between 30° to 70°. It should be observed that too great a deflection of the spray in the nasal valve 2 could have the effect of depositing fluid mainly, or totally, in the nasal valve, which would not be desirable. The parameters of the secondary flow, and in particular the flowrate, the speed, and the angle α of the secondary flow, should thus be adjusted and adapted to the spray generated by the dispenser system 20. Thus, depending on the kind of dispenser system 20, there may be variation in the parameters of the spray expelled through the spray orifice 35, such as the speed of the particles and their density, and consequently the parameters of the secondary flow should be adapted to each particular situation.

In order to verify the functioning of the invention, the shape of a spray, i.e. a plume, based on an aerosol of powder has been filmed with and without adding a secondary flow. The orientation of the secondary flow relative to the axis of the spray was about 80°. The flowrate of the secondary flow was adjusted to 15 liters per minute (L/min), and the diameter of the outlet orifice of the secondary flow channel was 0.9 mm, giving an outlet speed of the secondary flow of air of 393 meters per second (m/s).

Figure 4A:
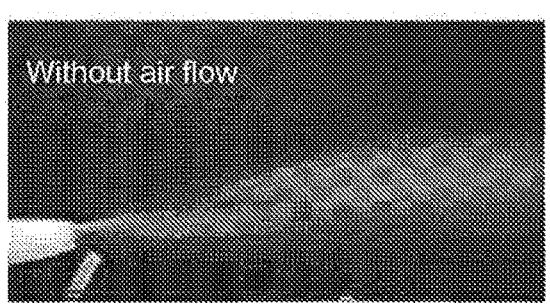
FIGS. 4a and 4b show the shapes of the spray, respectively with a prior-art nasal spray device and with a nasal spray device of the present invention.
Figure 4B:
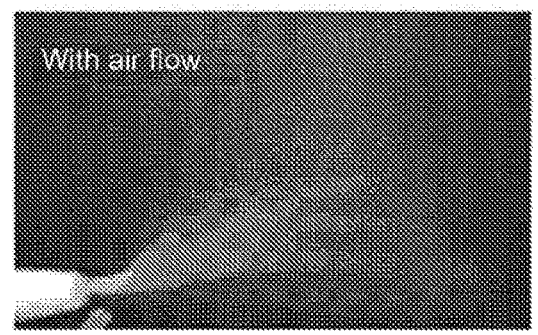

FIG. 4a shows a photograph of the conventional plume, without adding the secondary flow. FIG. 4b shows the shape of the plume when adding the secondary flow of the invention. The photographs clearly show a significant change in the shape of the plume, and the particles of the spray reach locations of the nasal cavity that are further away than the locations reached with a conventional plume, as shown very diagrammatically in FIGS. 1 and 2.

In order to verify whether the deflection of the path of the particles of the spray makes it possible to target the ethmoids, a nasal spray device 100 of the single-dose powder type was loaded with fluorescein and was tested on two nasal-cavity models, a man-type model and a woman-type model. The average outlet speed of the sprays was 33 m/s, with a minimum of 22 m/s and a maximum of 52 m/s (with the nasal spray device used for this test, the speed was dependent on the actuation force of the device). For the secondary flow, a sloping tube was added in the proximity of the spray orifice, which tube made it possible to generate the secondary flow with a speed of 393 m/s and an orientation of about 80°.

The deposition of particles of powder in the target zones was compared in both circumstances. For both tests, the same configurations were selected, i.e. in both circumstances the spray device was oriented at about 30° in the nostril and penetration into the nostril was similar. It should be observed that when adding the secondary flow there was clearly significant deposition in the tops of the ethmoids. However, without adding the secondary flow, the spray particles did not reach the ethmoids, and deposition was situated mainly in the bottom of the conchae and on the floors. When adding a secondary flow, the amount of particles deposited in the tops of the conchae compared to the total deposited was 3%, while it was 0% with the conventional device, without adding the secondary flow.

Other tests were performed on the man model comparing the deposition of powder obtained with the conventional device and the deposition obtained by adding secondary flows at different speeds (65.8 m/s and 262 m/s). Deposition in the ethmoids without secondary flow was 0%, deposition with a secondary flow having a speed of 65.8 m/s was 3.6%, and deposition with a secondary flow having a speed of 262 m/s was 10%. In other words, the faster the speed of the air compared to the speed of the particles of the spray, the more the particles follow the path of the secondary flow. It is thus possible to increase the deposition in the ethmoids by increasing the speed of the secondary flow relative to the speed of the spray. In order to avoid using secondary flows that are too strong, which could turn out to be uncomfortable for users, it is desirable to reduce the speed of the spray, which makes it possible to obtain the same effects with a weaker secondary flow.

Figure 5A:
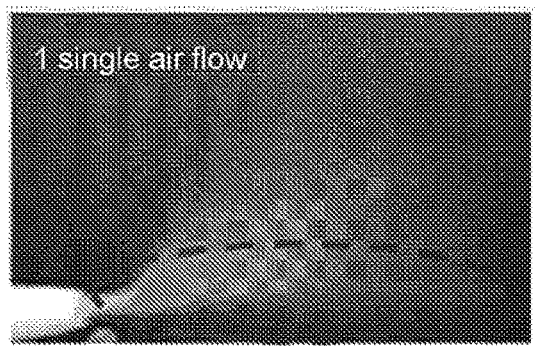
FIGS. 5a and 5b show the shapes of the spray with a nasal spray device of two embodiments of the present invention.
Figure 5B:
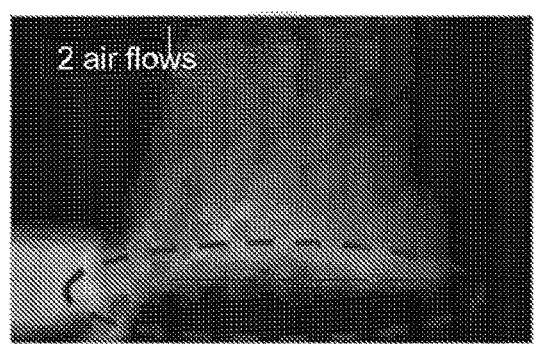

In addition, by adding a plurality of parallel secondary flows, the probability of the particles of spray following the desired path increases. FIGS. 5a and 5b show a comparison between the shape of the plume, still obtained with a spray device of the powder single-dose type, firstly when adding a single secondary flow (FIG. 5a), and secondly when adding two parallel secondary flows (FIG. 5b). A comparison of the bottom portions of the plumes show that adding a plurality of secondary flows causes a major portion of the particles of spray to follow the desired path. Specifically, in FIG. 5b, there are fewer particles of spray present in the bottom zone. This situation also corresponds to using a "film" type of air flow. The shape of the air-flow orifice may have a section that is circular, but it could equally well be elliptical or rectangular.

Another test was performed with a nebulizer. By adding a secondary flow (oriented at about 80°) to a nebulizer producing fine particles (1 μm to 10 μm), the secondary flow having an outlet speed that was faster than the speed of the spray (20 m/s compared to 16 m/s) and having an outlet-orifice with a section of the same order as the section of the spray orifice, the path and the shape of the plume was greatly affected by the flow of air. Specifically, deposition in the conchae increased significantly from 2.4% to 48.48%, and deposition in the floors reduced from 72.29% to 4.9%.

By adding a secondary flow having a speed of 26 m/s but coming out of a tube having an outlet-orifice section (2.2 square millimeters ($mm^2$)) that is smaller than the spray orifice section (3.2 $mm^2$), only a portion of the particles of spray were deflected. Specifically, in this circumstance, deposition in the conchae was increased by only 4.98%.

It thus appears to be desirable to add a secondary flow firstly having an outlet speed that is faster than the speed of the particles of spray. Secondly, the section of the outlet orifice of the secondary flow generator system should be at least of the same order as the section of the spray orifice of the spray, so that a major portion of the aerosols are deflected.

Figure 12:
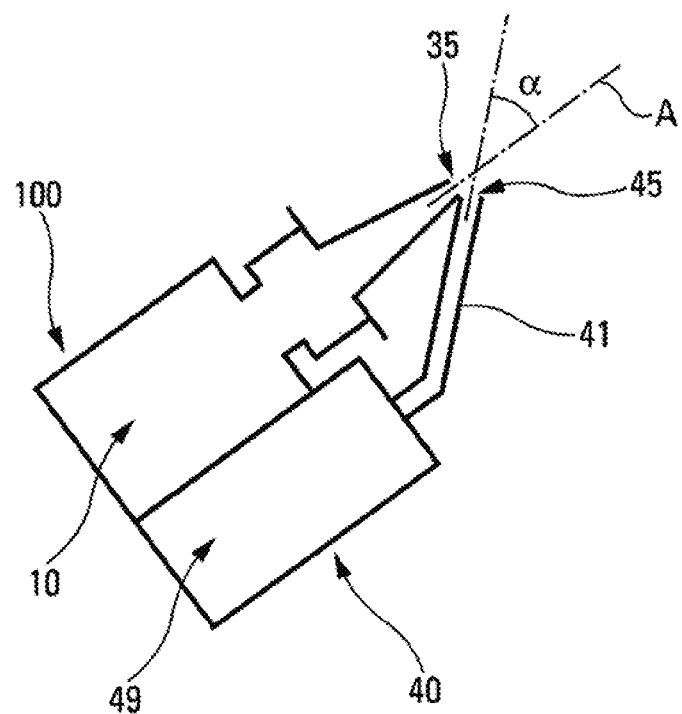
FIGS. 12 and 13 are views similar to the views in FIGS. 6 to 7, showing still another advantageous embodiment of the present invention.
Figure 13:
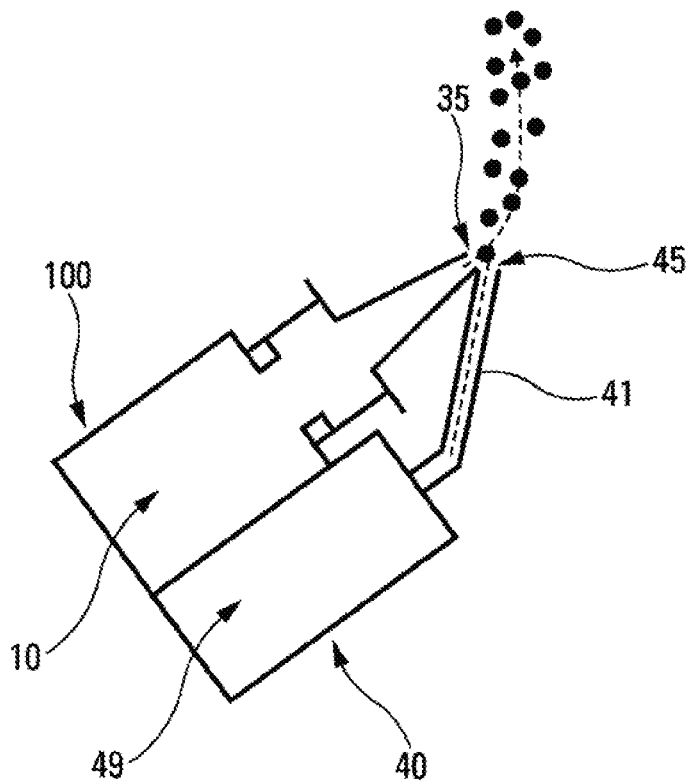

An embodiment of this invention is shown in FIGS. 12 and 13. In this configuration, the nasal spray device 100 is a nasal liquid-spray device provided with a spray orifice 35. The liquid medication is contained in the reservoir 10 and doses of medication in the form of a spray of particles are produced at the spray orifice 35, typically by means of a metering valve that functions with a propellant gas (not shown in the figures). The nasal spray device 100 is secured to a secondary flow generator system 40 that contains a propellant gas, typically a hydrofluoroalkane (HFA) gas, in its reservoir 49. Said reservoir 49 is connected to an outlet orifice 45 via a secondary flow channel 41. The outlet orifice 45 of said secondary flow generator system 40 is arranged axially downstream from said spray orifice 35 of said nasal spray device 100, and forms therewith an angle alpha (α), e.g. of 45°. Thus, while the nasal spray device 100 is being actuated manually, as shown in FIG. 13, the secondary flow generator system 40 that is secured to said nasal spray device 100 is also triggered automatically, so as to produce a dose of HFA gas that is delivered through the outlet orifice 45 simultaneously with the dose of medication in the form of spray being dispensed through the spray orifice 35. The HFA gas is directed by the outlet orifice 45 of the secondary flow generator system 40 along said angle α relative to the axis of the spray orifice 35. Thus, downstream from said spray orifice 35, the particles of liquid are subjected not only to their initial speeds along the axis A, but also to the secondary flow of gas coming from the outlet orifice 45 of the secondary flow generator system 40. The particles are thus directed towards the roofs of the nasal cavities.

Comparative tests have demonstrated that the orientation of the device of the invention in the user's nostril, in particular when the device is made in accordance with FIGS. 12 and 13, can have an influence on the effectiveness of the device. The tests have also revealed differences between men and women, and differences depending on the depth to which the device was inserted into the nostril during use.

Figure 14:
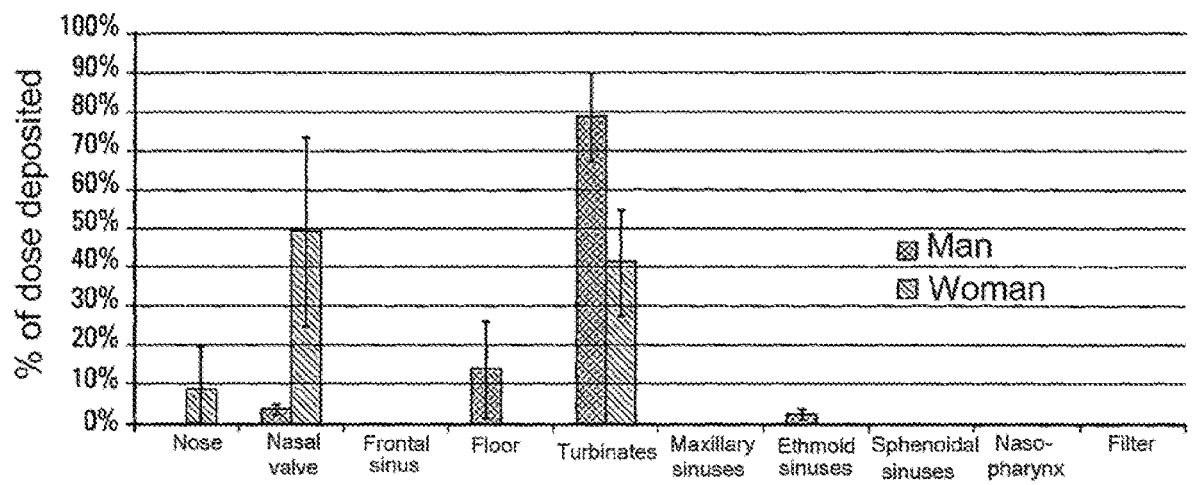
FIG. 14 is a bar chart showing spray deposition in the various zones of the nostril for a man and for a woman, using a device made and oriented as shown in FIGS. 12 and 13, i.e. with the flow of air deflecting the spray upwards.

FIG. 14 is a thus a bar chart showing the amounts of spray deposited in various zones of the nostril, firstly for a man and secondly for a woman, when using a device made and oriented as in FIGS. 12 and 13, i.e. with the flow of air deflecting the spray upwards. The optimum angle alpha (α) turned out to be 30°. The chart shows that spray deposition on the ethmoids was only 2.7% (±0.1%) in men and almost zero (0.2%±0.1%) in women. In particular, this may be explained by the fact that in some anatomies, the turbinates protect the ethmoids, like a screen, against an upwardly deflected spray.

Figure 15:
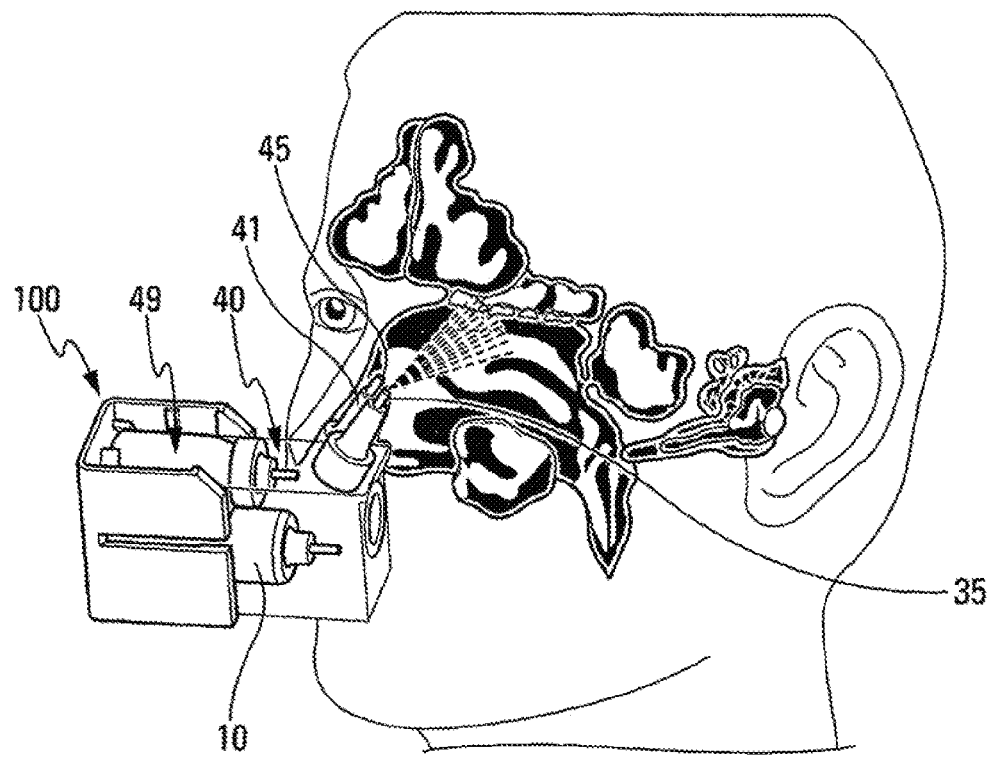
FIG. 15 is a diagrammatic representation of a device made in accordance with FIGS. 12 and 13, but differently oriented in the nostril, with the flow of air deflecting the spray sideways.
Figure 16:
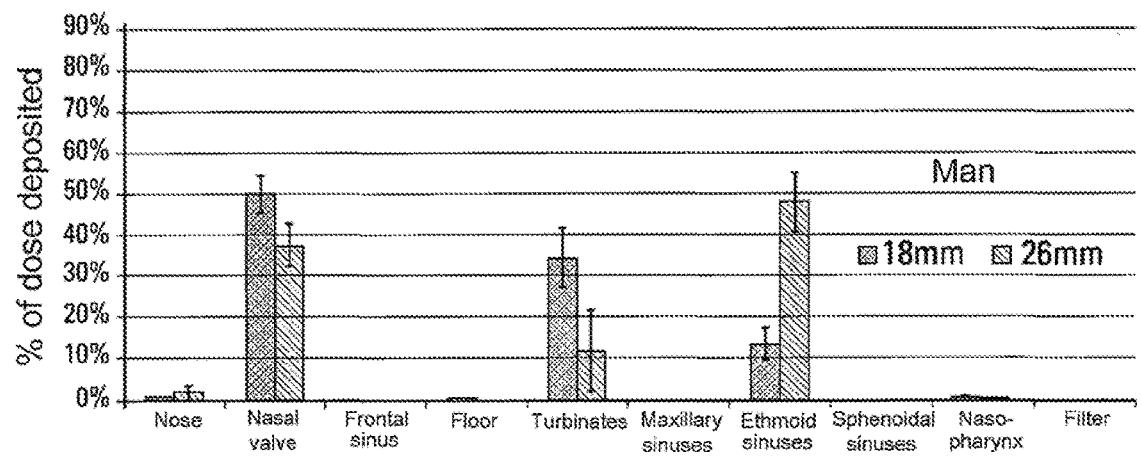
FIG. 16 is a bar chart showing spray deposition in the various zones of the nostril for a man model, using a device made and oriented as shown in FIG. 15, and comparing two depths of insertion into the nostril.
Figure 17:
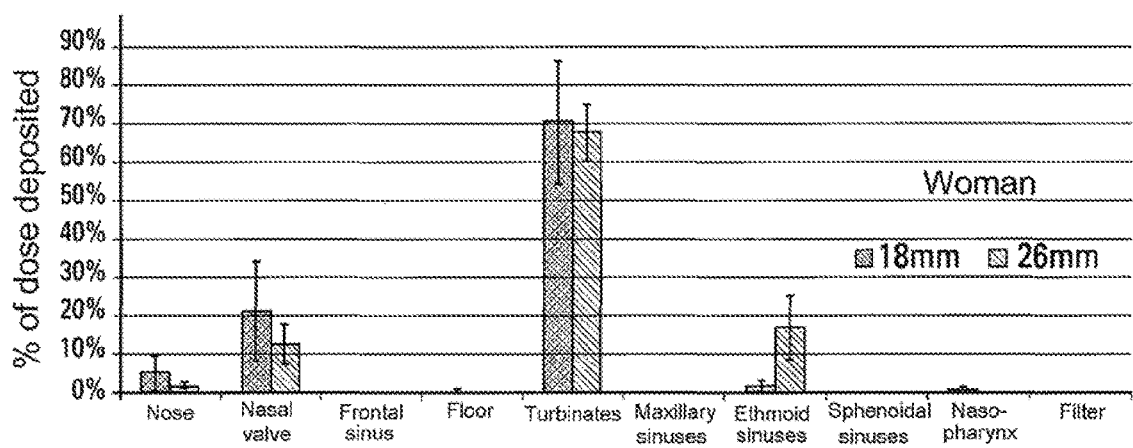
FIG. 17 is the same bar chart as the bar chart in FIG. 16, but for a woman model.

Comparative tests have thus been performed with a different orientation, namely with the flow of air deflecting the spray sideways, as shown in FIG. 15. The optimum angle alpha (α) turned out to be 45°. FIGS. 16 and 17 show the results obtained with the FIG. 15 orientation, respectively for a man model and for a woman model, and by comparing two depths of insertion into the nostril, one of 18 mm and the other of 26 mm.

In FIG. 16, it should be observed that, for the man model, spray deposition on the ethmoids reached 13.9% (±3.7%) with a standard insertion depth, and even 48.3% (±7.1%) with an increased insertion depth. In FIG. 17, the same applies for the woman model, in which spray deposition on the ethmoids reached 2.2% (±1.3%) with a standard insertion depth, and 17.4% (±8.3%) with an increased insertion depth.

The tests thus demonstrate that it is preferable to deflect the spray sideways in the nostril rather than upwards, and that inserting the device deeper into the nostril is also beneficial for reaching the ethmoids. Thus, insertion of at least 15 mm seems desirable, while insertion of more than 30 mm could present risks of discomfort and/or injury for the user. Advantageously, the depth of insertion thus lies in the range 15 mm to 30 mm.

In all of the above-mentioned circumstances, the use of an external source of gas was necessary to generate the secondary flow(s). The secondary flow generator system is thus said to be "active". The source of gas may be an air expeller that compresses air by means of a piston, a small gas cylinder similar to those used for metered dose inhalers (MDIs) containing an HFA gas, or an air compressor for a nebulizer.

Another application of the present invention relates to the use of a nasal spray device associated with a secondary flow generator system of the passive type, i.e. in which the secondary flow is not generated by an external source, but merely by the user inhaling. In this situation, it is thus the user who inhales that creates the secondary flow.

Figure 6:
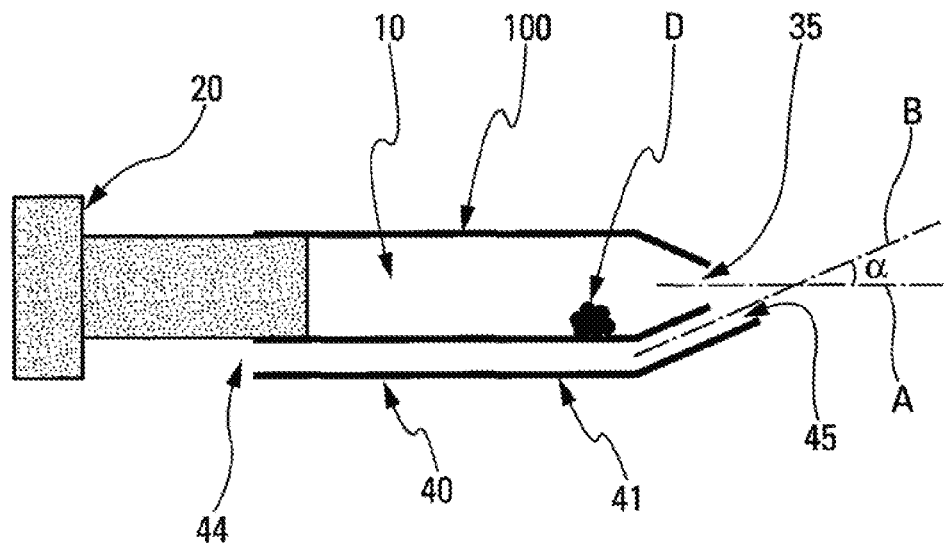
FIGS. 6 and 7 are very diagrammatic views of a nasal spray device in an advantageous embodiment of the present invention, respectively before the fluid is sprayed and while the fluid is being sprayed.
Figure 7:
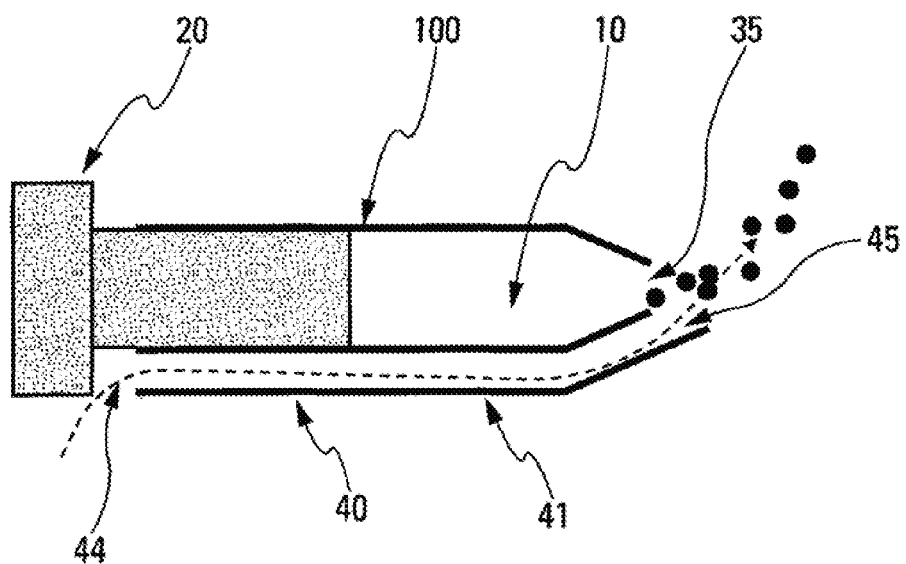

FIGS. 6 and 7 show, in very diagrammatic manner, an embodiment of the invention with such a secondary flow generator system of the passive type. The nasal spray device 100 includes a reservoir 10 containing a dose D of fluid, in particular in powder form. A dispenser system 20 forming an aerosol generator comprises a piston that slides in said reservoir 10 between a position prior to actuation shown in FIG. 6, and an actuated position shown in FIG. 7. At its axial end, the nasal spray device 100 includes a spray orifice 35 that advantageously has a diameter of 2 mm, for inserting into the nostril of the patient. The nasal spray device 100 further includes a secondary flow generator system 40 comprising a secondary flow channel 41 that is provided with an inlet orifice 44 and with an outlet orifice 45. The inlet orifice 44 is connected to the atmosphere and is for causing air to penetrate, from the outside, into the channel 41. The outlet orifice 45, that advantageously also has a diameter of 2 mm, is for delivering a secondary flow of air into the spray coming from the spray orifice 35, so as to deflect the particles of spray from their substantially axial path. In this embodiment, the angle α is advantageously 35°.

Thus, when the user inhales by nasal inhalation, the inhaled flow of air penetrates into the channel 41 and is then directed along an angle of 35° through the outlet orifice 45. During this inhalation stage, the user presses on the piston of the dispenser system 20, which generates a flow of compressed air in the reservoir 10 for generating an aerosol and expelling the dose of powder D, in the form of a spray of particles, through the spray orifice 35. Thus, downstream from the spray orifice 35, the particles of powder are subjected not only to their initial speeds along the axis A, but also to the secondary flow of air coming from the outlet orifice 45 of the channel 41, which deflects them away from their path along a non-axial direction, as can be seen in FIG. 7. The particles of powder are thus directed towards the roofs of the nasal cavities.

An advantage of this embodiment lies in not using an external source of gas or air under pressure, and in adding only a simple mechanical element, namely the channel 41, to existing nasal spray devices.

Comparative tests between a standard device and a device made in accordance with the embodiment in FIGS. 6 and 7 have shown the effectiveness of the invention: powder deposition on the ethmoids obtained with the conventional device was 0%, whereas with a secondary flow of air generated by the user inhaling, deposition lay in the range 3.5% to 7.8%, depending on the flowrate of the inhalation flow that was typically about 30 L/min.

Figure 8:
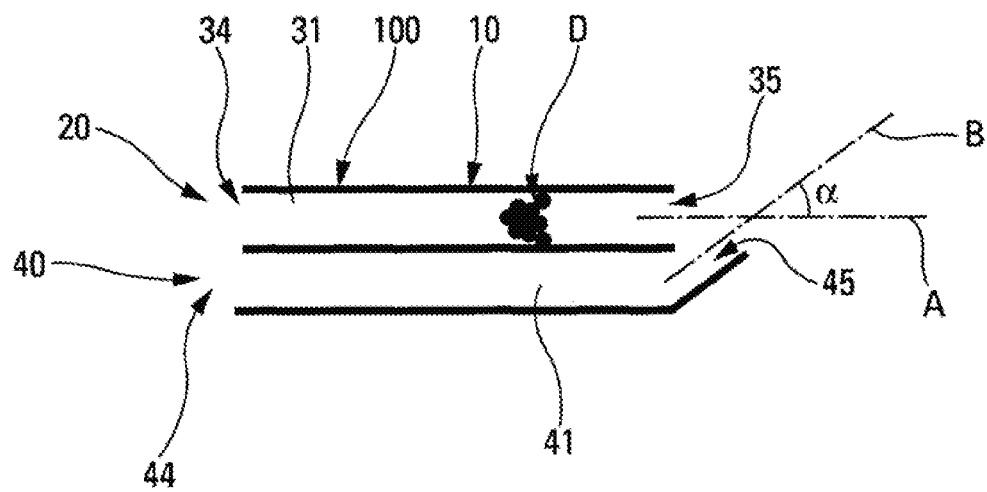
FIGS. 8 and 9 are views similar to the views in FIGS. 6 to 7, showing another advantageous embodiment of the present invention.
Figure 9:
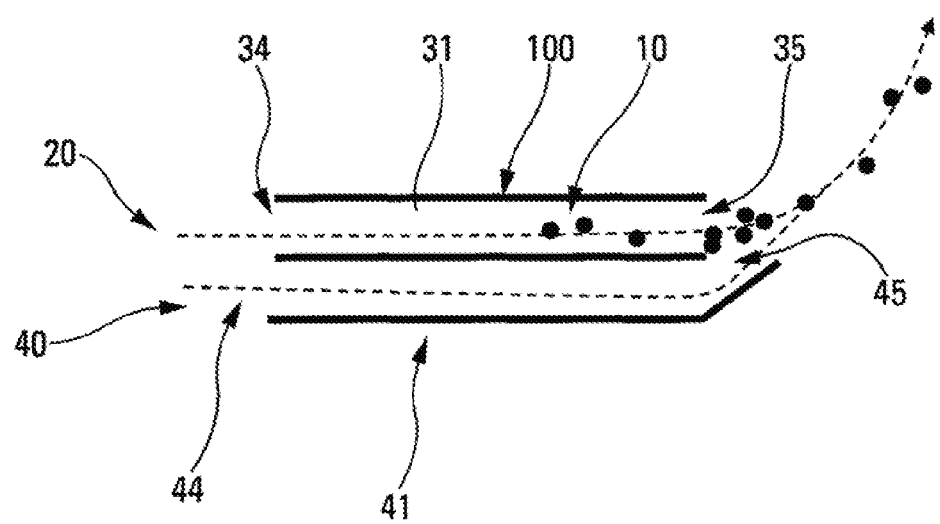

FIGS. 8 and 9 show another embodiment of the invention with a secondary flow generator system of the passive type.

In this embodiment, the device 100 comprises a reservoir 10 containing a dose of powder D, the reservoir forming a duct 31 that includes an inlet orifice 34 for causing the air to penetrate from the outside of the duct 31 to its inside, and a spray orifice 35, advantageously having a diameter of 2 mm, for expelling the dose of powder in the form of spray into the user's nostril. The duct 31, with its inlet and spray orifices 34, 35 thus form the dispenser system 20 in this embodiment. The device 100 includes a channel 41 that includes an inlet orifice 44 for causing the air to penetrate from the outside of the channel 41 to its inside, and an outlet orifice 45, advantageously having a diameter of 2 mm, for delivering a secondary flow of air into the spray of particles, so as to deflect the particles away from their substantially axial path. In this embodiment, the angle α is advantageously 35°.

While the user is inhaling, the inhaled air passes through the two inlet orifices 34 and 44 so as to penetrate respectively into the duct 31 forming the reservoir 10, and into the channel 41. The air passing through the duct 31 transports the particles of powder to the spray orifice 35. Simultaneously, the air passing through the channel 41 is directed to the outlet orifice 45. Thus, at the outlet of the spray orifice 35, the particles of powder are subjected not only to their substantially axial initial speed, but also to the secondary flow of air coming from the outlet orifice 45, which deflects them away from their substantially axial initial path, as can be seen in FIG. 9. The particles of powder are thus directed towards the roofs of the nasal cavities.

An advantage of this configuration lies in not using an external source of gas or air under pressure, and in adding only a simple mechanical element, namely the channel 41, to existing nasal spray devices. In addition, the system is completely passive, since both the dispenser system 20 and the secondary flow generator system 40 are of the passive type. Furthermore, the dispenser system 20 and the secondary flow generator system 40 are synchronized automatically and naturally merely by the user inhaling.

Figure 10:
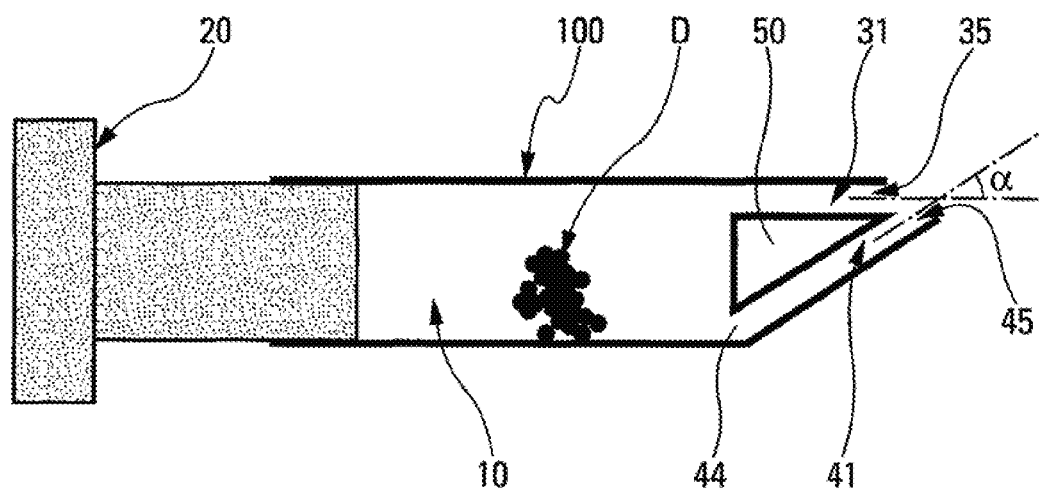
FIGS. 10 and 11 are views similar to the views in FIGS. 6 to 7, showing another advantageous embodiment of the present invention.
Figure 11:
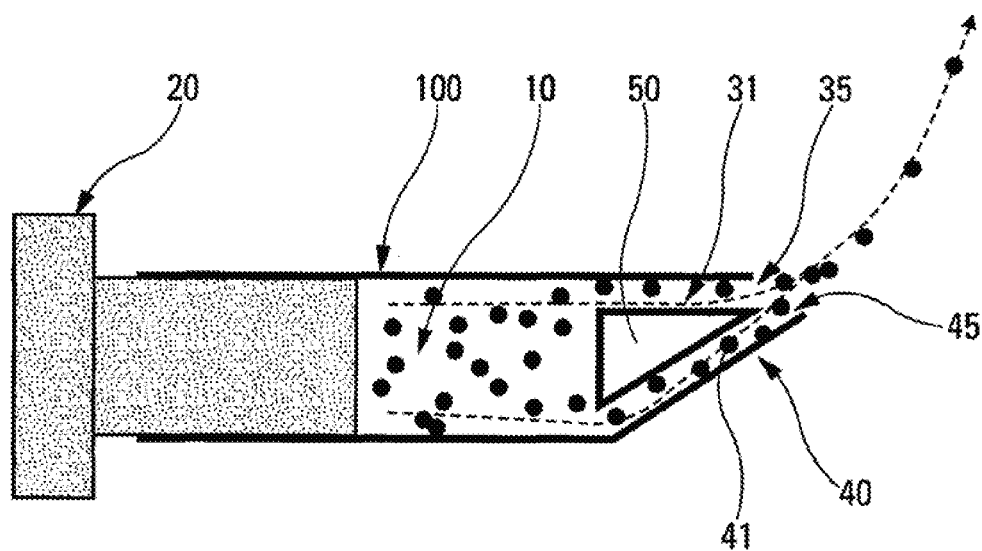

FIGS. 10 and 11 show still another embodiment of the invention. The embodiment differs from the embodiments described above in that the secondary flow is formed only of gas, in particular air, but comprises, as the spray, a mixture of gas, in particular air, and of fluid, in particular particles of powder.

The nasal spray device 100 includes a reservoir 10 containing a dose D of fluid, in particular in powder form. A dispenser system 20 forming an aerosol generator comprises a piston that slides in said reservoir 10 between a position prior to actuation shown in FIG. 10, and an actuated position shown in FIG. 11. Unlike the embodiment in FIGS. 6 and 7, in this embodiment the secondary flow generator system 40 is not separate from the dispenser system 20, but, on the contrary, it is the same piston that generates both the spray that is expelled through the spray orifice 35 and also the secondary flow of air that is expelled simultaneously through the outlet orifice 45. To do this, the reservoir 10 contains a separator 50, arranged upstream from the spray orifice 35, that, during actuation, acts within the reservoir to separate the powder and compressed air mixture into two flows, one flowing into an axial duct 31 towards the spray orifice 35, and the other flowing into a sloping channel 41 towards the outlet orifice 45. Advantageously, both the spray orifice 35 and the outlet orifice 45 have a diameter of about 2 mm. The slope of the channel 41, and thus the angle α, is advantageously about 35°.

Thus, during actuation, the user pushes the piston into the reservoir 10, and this compresses the air and enables the dose of powder D to be put into an aerosol inside the reservoir 10. The separator 50 separates the aerosol into two flows that flow respectively in the duct 31 and in the channel 41. Thus, downstream from the spray orifice 35, the particles of powder are subjected not only to their substantially axial initial speed, but also to the secondary flow of air and of particles coming from the outlet orifice 45, which deflects them away from their axial path, as can be seen in FIG. 11. The particles of powder are thus directed towards the roofs of the nasal cavities.

An advantage of this embodiment lies in not using an external source of gas or air under pressure, and in adding only a simple mechanical element, namely the separator 50, to existing nasal spray devices.

An advantage of the present invention, whatever its embodiment, is to improve the deposition of fluid in the nasal cavities, in particular at the ethmoid sinuses, substantially without having to modify the properties of existing sprays. Specifically, the speed of the particles, their sizes, and other properties of the spray, need not be modified as a result of the present invention, the addition of a secondary flow after the spray orifice of the conventional spray being sufficient to reach the ethmoid sinuses. In particular, this enables the invention to be made with a device that is small and that can be carried in a pocket.

It should be observed that the embodiments described above in FIGS. 6 and 11 do not include a spray profile upstream from the spray orifice, the fluid being in powder form and being put into an aerosol inside the reservoir 10. However, naturally each of these embodiments could also function with such a spray profile, e.g. associated with a conventional fluid dispenser pump, in particular when the fluid is in liquid form. By way of example, this may be the situation with spray devices, as described in FIGS. 12 and 13, inhaler devices of the "soft mist" type such as the Respimat® by Boehringer-Ingelheim, and jet, ultrasonic, or mesh nebulizers.

In addition, in the embodiments described above, the outlet orifice 45 of the secondary flow generator system 40 is arranged in contact with the spray orifice 35, but the outlet orifice could be offset a little, axially and/or laterally, relative to said spray orifice. In particular, the two orifices 35 and 45 are not necessarily formed on the same part of the nasal spray device 100. Furthermore, the device may be oriented in any way in the nostril, with however a preferred orientation that consists in deflecting the spray sideways in the nostril.

The present invention is described above with reference to several advantageous embodiments, but naturally any useful modification could be applied thereto by a person skilled in the art, without going beyond the ambit of the present invention, as defined by the accompanying claims.

The invention claimed is:

1. A nasal fluid-spray device (100) comprising: a reservoir (10) containing at least one dose (D) of fluid; and a dispenser system (20) that, each time the device is actuated, sprays a dose (D) of fluid through a spray orifice (35) configured to be locate inside a user's nostril during actuation of the nasal fluid-spray device and to generate a spray that extends axially from said spray orifice (35); said device (100) further comprises a generator system (40) for generating a secondary flow, which generator system is actuated simultaneously with said dispenser system (20), said secondary flow generator system (40) comprising a secondary flow channel (41) that is provided with an outlet orifice (45), said outlet orifice (45) being arranged downstream from said spray orifice (35) in the axial direction of said spray, and said secondary flow extending from said outlet orifice (45) along an axis (B) that forms an angle (a) relative to the axis (A) of said spray and that intersects said axis (A); and wherein the secondary flow generator system is operatively configured to cooperate with the spray so that, in use with the spray orifice located inside the user's nostril, the spray exits the device through said spray orifice and initially enters into the nostril in an axial direction and is then deformed or deflected or both only outside the device and inside the nostril.

2. The device according to claim 1, wherein said secondary flow of said secondary flow generator system (40) is formed by an external source of compressed gas.

3. The device according to claim 1, configured to generate said secondary flow of said secondary flow generator system (40) when the user inhales through the device.

4. The device according to claim 1, wherein said secondary flow of said secondary flow generator system (40) is made up of gas.

5. The device according to claim 1, wherein said secondary flow of said secondary flow generator system (40) comprises air mixed with particular particles of powder.

6. The device according to claim 1, wherein said angle (a) lies in a of range 10° to 90°.

7. The device according to claim 1, wherein the diameter of said spray orifice (35) is substantially identical to the diameter of said outlet orifice (45).

8. The device according to claim 1, wherein the diameter of said spray orifice (35) is less than the diameter of said outlet orifice (45).

9. The device according to claim 8, wherein the diameter of said spray orifice (35) is 0.3 mm and the diameter of said outlet orifice (45) is 0.4 mm.

10. The device according to claim 1, wherein said secondary flow channel (41) of said secondary flow generator system (40) includes an inlet orifice (44).

11. The device according to claim 10, wherein said inlet orifice (44) is connected to a source of compressed gas.

12. The device according to claim 10, wherein said inlet orifice (44) is connected to the atmosphere.

13. The device according to claim 1, wherein said fluid is a medication in powder form.

14. The device according to claim 1, wherein said fluid is a medication in liquid form.

15. The device according to claim 1, wherein said spray is composed of particles having a diameter that lies in the range 1 μm to 500 μm.

16. The device according to claim 1, configured such that said secondary flow deforms and/or deflects said spray sideways in the user's nostril.

17. The device according to claim 1, wherein, during actuation, said spray orifice (35) is inserted into the nostril to a depth that lies in the range 15 mm to 30 mm.

18. The device according to claim 4, wherein said gas is air.

19. The device according to claim 1, wherein said angle lies in the range of 20° to 80°.

20. The device according to claim 1, wherein said angle lies in the range of 30° to 70°.

21. The device according to claim 1, wherein the spray orifice directly opens to an outside of the device such that the spray exiting the spray orifice immediately exits the device and is deformed by the secondary flow.

* * * * *